US012629594B2

(12) United States Patent
Uppuluri et al.

(10) Patent No.: US 12,629,594 B2
(45) Date of Patent: May 19, 2026

(54) AUTOMATED DETECTION OF VISUAL IMPAIRMENT AND ADJUSTMENT OF SETTINGS FOR VISUAL IMPAIRMENT

(71) Applicant: Sony Interactive Entertainment Inc., Tokyo (JP)

(72) Inventors: Satish Uppuluri, Dublin, CA (US); Jason Grimm, Sunnyvale, CA (US); Elizabeth Ruth Juenger, San Francisco, CA (US); Ryan Sutton, Venice, CA (US)

(73) Assignee: Sony Interactive Entertainment Inc., Tokyo (JP)

( * ) Notice: Subject to any disclaimer, the term of this patent is extended or adjusted under 35 U.S.C. 154(b) by 209 days.

(21) Appl. No.: 17/890,160

(22) Filed: Aug. 17, 2022

(65) Prior Publication Data

US 2024/0058698 A1      Feb. 22, 2024

(51) Int. Cl.
| | |
|---|---|
| *A63F 13/533* | (2014.01) |
| *A61B 3/024* | (2006.01) |
| *A61B 3/032* | (2006.01) |
| *A61B 3/06* | (2006.01) |
| *A61B 3/18* | (2006.01) |
| *A63F 13/52* | (2014.01) |
| *A63F 13/80* | (2014.01) |

(52) U.S. Cl.
CPC ............ *A63F 13/533* (2014.09); *A61B 3/024* (2013.01); *A61B 3/032* (2013.01); *A61B 3/066* (2013.01); *A61B 3/18* (2013.01); *A63F 13/52* (2014.09); *A63F 13/80* (2014.09); *A63F 2300/308* (2013.01); *A63F 2300/8094* (2013.01)

(58) Field of Classification Search
None
See application file for complete search history.

(56) References Cited

U.S. PATENT DOCUMENTS

| | | | |
|---|---|---|---|
| 2006/0139312 A1 | 6/2006 | Sinclair et al. | |
| 2018/0140178 A1 | 5/2018 | Anderson et al. | |
| 2021/0252403 A1* | 8/2021 | Stevens | A63F 13/85 |
| 2022/0366131 A1* | 11/2022 | Ekron | G06F 9/453 |
| 2023/0385983 A1* | 11/2023 | Kvasnica | G06N 20/00 |
| 2024/0180416 A1* | 6/2024 | Gonzalez Garcia | A61B 3/0091 |

FOREIGN PATENT DOCUMENTS

WO     WO 2022226141     * 10/2022  ........... A61B 3/0204

OTHER PUBLICATIONS

"Visual field" Vision and Eye Health, Accessed Jul. 29, 2022. Available at: https://www.vision-and-eye-health.com/visual-field.html.
International Search Report and Written Opinion for International Application No. PCT/US2023/026264, dated Oct. 17, 2023.

* cited by examiner

*Primary Examiner* — Ifedayo B Iluyomade
(74) *Attorney, Agent, or Firm* — Kilpatrick Townsend & Stockton LLP

(57) ABSTRACT

A method, system and computer program product for automated visual setting importation is disclosed. A first application running on a first device requests a vision setting for a second application. A vision setting of the first application running on a first device is determined to correspond to the vision setting for the second application. The vision setting for the second application is then applied to the corresponding vision setting of the first application.

24 Claims, 8 Drawing Sheets

AUTOMATED DETECTION OF VISUAL IMPAIRMENT AND ADJUSTMENT OF SETTINGS FOR VISUAL IMPAIRMENT

FIELD OF THE DISCLOSURE

Aspects of the present disclosure are related to adjustment of device settings for visual impairment, specifically aspects of the present disclosure relate to detection of visual impairment and importation of visual impairment settings.

BACKGROUND OF THE DISCLOSURE

Operation of applications running on a computing device is an audio-visual experience. Visuals are often the most important method of interaction with the application and the computing device. Applications ordinarily utilize visual communications such as text, video and graphical animations, to provide information to the user. Visual communication in applications often uses small size fonts, small icons and color coding to provide information to the user.

The reliance on the use of visual communications sometimes makes operation of applications and devices difficult for visually impaired users. Visually impaired users may suffer from a variety of different conditions that effect interactions with applications and devices. Some users may be near sighted or far sighted which may affect the size or distance at which text and/or images displayed on the screen are intelligible to the user. Some users may be colorblind. There are three different types of colorblindness red-green colorblind Blue-yellow colorblind and complete colorblindness. Within the category of red-green color blindness there are two subgroups, Deuteranomaly which makes green look more red, and Protanomaly which makes red look green and reduces the brightness of reds. Blue-yellow color blindness also includes two categories, Tritanomaly which makes it difficult to distinguish between blue and green and between red and yellow, and Tritanopia is the inability to discern between blue and green and between purple and red and between yellow and pink, it also makes all colors less bright. Finally complete colorblindness is the inability to see colors at all, it is also known as monochromacy. Other vision impairments may include blind spots or lack of peripheral vision. These issues may require the user to move their device to a place where they have vision and may adversely affect users of heads mounted displays.

Recently, application developers have added tools to improve the accessibility of applications and devices for visually impaired users. Modern applications often have settings that allow users to change the size of type font, magnify portions of the screen, have text read aloud, change color for color blindness, enlarge icons and change screen resolution. Currently there is no standard for accessibility settings between applications and users must set their preferred settings within each application individually.

Additionally, some users may not realize that they have any vision impairment at all. Users with impaired vision may attribute their difficulties using applications to the design of the application or may adjust visual settings for an application or device without realizing they have a particular impairment.

It is within this context that aspects of the present disclosure arise.

BRIEF DESCRIPTION OF THE DRAWINGS

The teachings of the present disclosure can be readily understood by considering the following detailed description in conjunction with the accompanying drawings, in which.

DESCRIPTION OF THE SPECIFIC EMBODIMENTS

Although the following detailed description contains many specific details for the purposes of illustration, anyone of ordinary skill in the art will appreciate that many variations and alterations to the following details are within the scope of the invention. Accordingly, the exemplary embodiments of the invention described below are set forth without any loss of generality to, and without imposing limitations upon, the claimed invention.

According to aspects of the present disclosure a user's experience using an application may be improved through the use of vision settings from other applications and diagnosis of visual impairments through interactive games. Applications running on a user's device each may have vision settings set by the user. Each application may have its own vision settings that differ slightly from each other. For example, and without limitation, an operating system (OS) may have settings for the size of font, icon size and magnification and a videogame may have settings for user interface (UI) size and cursor or crosshair size. Vision settings in one application therefore may not have a direct correspondence to vision settings in a second application. As such, to properly import a setting from the second application to the first application it may be useful to determine the relationship between the visual settings of the first and second applications. Once a relationship has been determined settings of the second application that are identical or similar to corresponding settings in the first application may be applied to the first application. Additionally, in some implementations the settings values may be modified to be compatible with the first application.

In some implementations, the second application may be a vision test game configured to test the user for one or more vision impairments. The results of the vision test game may be vision settings of the second application. The vision settings from the test game may be imported into the first application and the user may be notified that they have a vision impairment. This may improve the user's experience as vision settings may be enabled or changed to suit their particular impairment. Additionally, users may not realize they have a visual impairment and the vision test games may provide a convenient tool to improve the user experience without having a professional optometrist diagnose the user.

Figure 1:
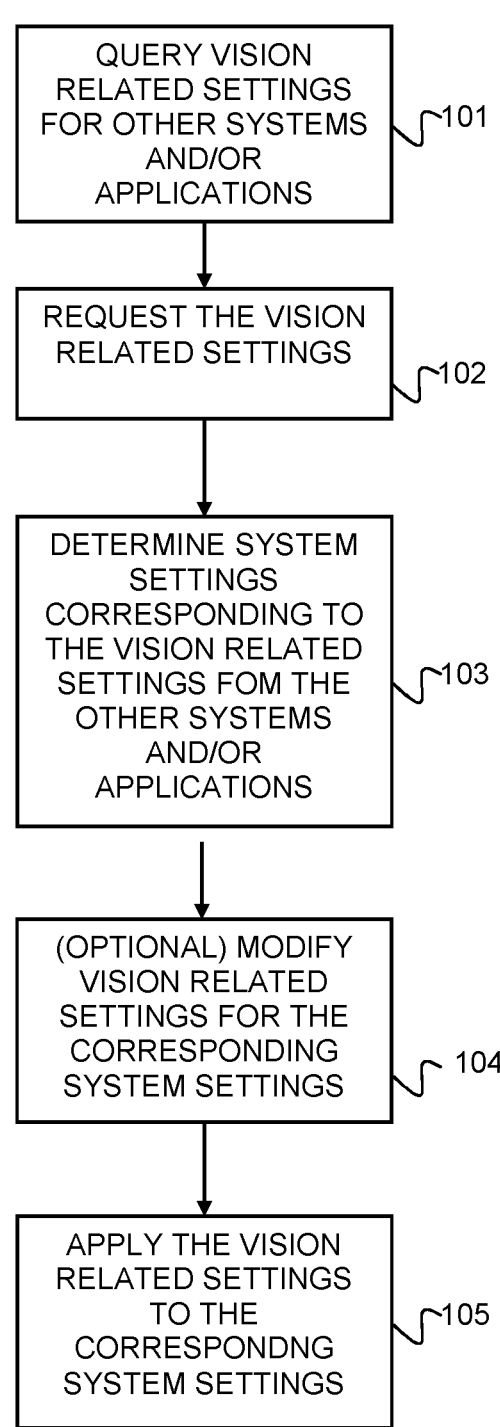
FIG. 1 is a flow diagram depicting a method for automated visual setting importation according to aspects of the present disclosure.

FIG. 1 depicts a method for automated visual setting importation with a first application according to aspects of the present disclosure. Initially the first application may query the second application for vision settings as shown at 101. The second application may include an application interface that provides meta information about the second application such as vision settings, application type, and similar to the first application. The second application may respond to the first application's query with vision related settings used by the second application. In some implementations the first application may have a list or database of vision related settings that other applications may implement. The first application may send a query to the second application asking if the second application has one or more of the settings on the list or database. Alternatively, the list or database may provide the settings to request based on the application or application type.

The first application may select which particular second application to query in a number of different ways. For example, the first and second applications may be stored in a memory or mass storage on a common device belonging to a given user. Alternatively, the first and second applications may be stored in different memories or mass storages associated with different devices or systems but are otherwise linked somehow to a common user, e.g., through a user account. Furthermore, the first and second devices may be interoperable with a common operating system or may be part of a common suite of applications. Independent of the nature of the association between the first and second applications, the nature of the query is generally that the first application somehow determines what visual settings are used by the second application. As a secondary matter, the query may involve locating the data corresponding to the values of the visual settings, e.g., determining where the values are stored in memory or mass storage.

According to certain aspects of the present disclosure, the first and second applications may be associated with different operating systems (OS). For example, a settings importation system or software may be configured to detect the settings of an application on one OS (e.g., Android or iOS) and then automatically apply those settings to programs on a different OS, e.g., PC Applications (Windows/MacOS), Console/PSS, etc. Alternatively, the software or system may ask users if they want to apply the settings.

Once the vision settings used by the second application have been determined the first application may request the vision setting values at 102. In particular, the first application may request vision setting values that have counterpart values for the first application. The second application may send the requested vision settings and vision setting values to the first application. Alternatively, the first application may read the vision setting values provided through the application interface. The device may determine the settings of the first application that correspond to the received settings of the second application as shown at 103. For example, and without limitation a font size set by the user on a second application may be determined to be related to a UI size of the first application and the setting of font size of the second application.

Next, in some optional implementations the values of the settings from the second application may be modified to be compatible with the first application settings as shown at 104. For example, and without limitation the second application may have a font size with three settings e.g. small, medium, large, whereas the second application may use point sizes for the UI font, the Font sizes from the second application may be modified by converting the qualitative font size to a quantitative font size by for example choosing a point font size that approximate the size of the font in the second application or dividing the range of font point sizes into three discrete sizes to match the three qualitative measurements of fonts on the second device. Finally, the (optionally) modified values of the vision related settings may be applied to the first application as depicted at 105.

Figure 2:
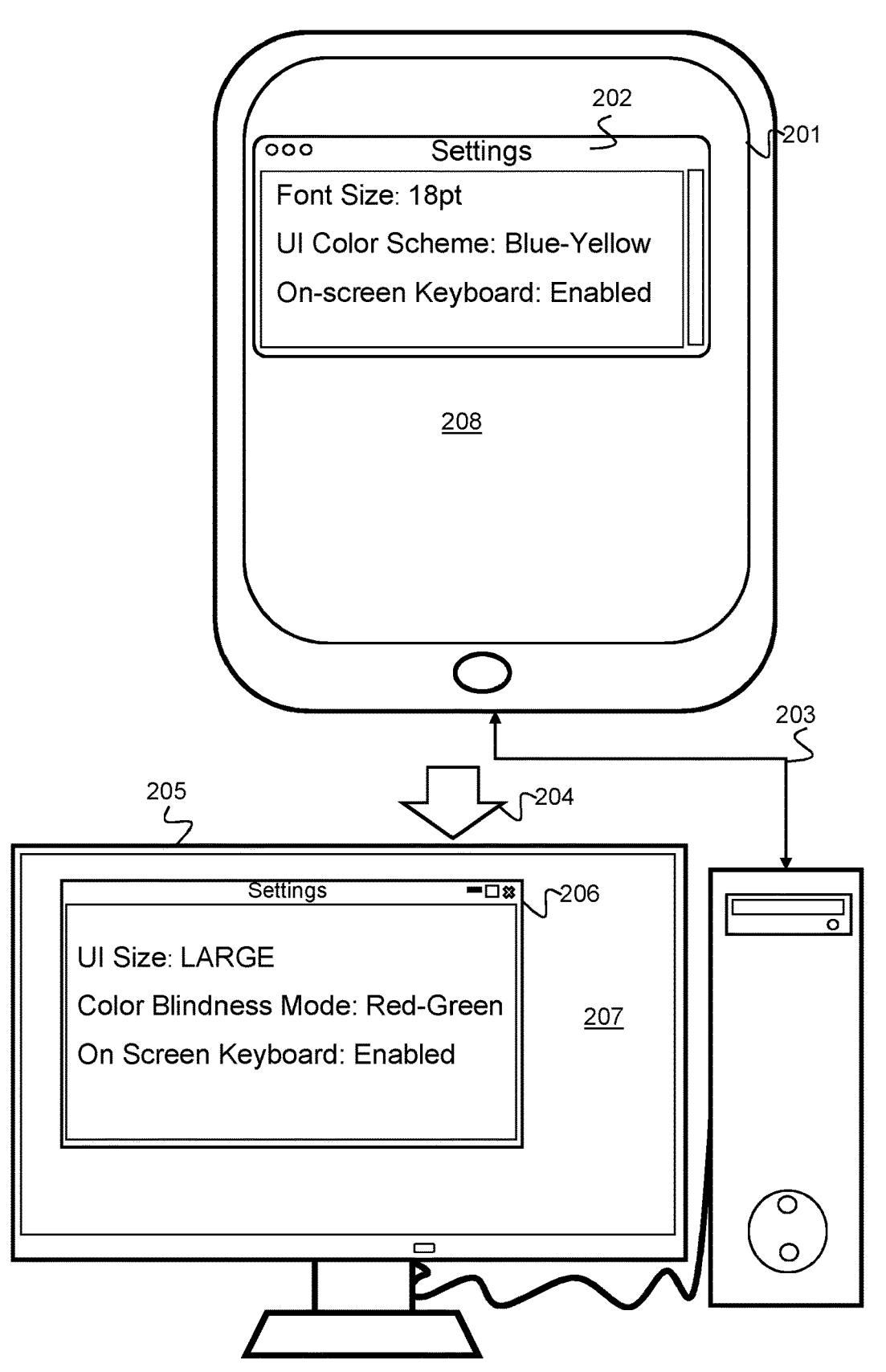
FIG. 2 is a graphical diagram showing an example implementation of automated visual setting importation according to aspects of the present disclosure.

FIG. 2 graphically depicts an example implementation of automated visual setting importation with a first application according to aspects of the present disclosure. In the implementation shown, a first application 207 runs on a first device 205. The first device 205 may be for example and without limitation, a personal computer (PC), game console, handheld tablet computer, e-reader, smartphone, or similar. The first device 205 may be in communication 203 with a second device 201 running a second application 208. Here the first application 207 may be for example and without limitation an operating system, a video game, a web browser, a word processor or similar. Likewise, the second application 208 may be for example and without limitation an operating system, a video game, a web browser, a word processor or similar. The second application and first application may be different from, or incompatible with each other. As such one or more settings from the second application 202 may not be directly related, compatible or functional with the settings of the first application 206.

According to aspects of the present disclosure, the first or second application may include an interface that displays the relevant settings, the application type, and the like. Such an interface may be used, for example, for users to confirm whether they want to update the settings of the second application to match the common settings across both applications.

In the example shown in FIG. 2, the settings of the first application 207 are shown without limitation to include UI size, color blindness mode and an on-screen keyboard. The settings of the second application 202 are shown to include without limitation font size, U.I. color Scheme, and an on-screen keyboard. Additional settings may include, but are not limited to, Zoom, Voice Over/Screen Reader, High Contrast, Reduced Motion and Animation, Bold Text, Color Inversion, and Closed Captions As shown, during automated importation settings from the second application 208 may be received 204 by the first application 207. The first device 205 may determine settings from the second application that correspond to settings of the first application. For example, and without limitation, the on-screen keyboard settings from the second application are determined to directly correspond to the on-screen keyboard settings of the first application with the exact same setting label. Some settings may have different labels but a simple correspondence, as shown, the U.I. Scheme of the second application includes a setting value for a Blue-Yellow U.I. scheme, a Blue-Yellow color scheme is easily seen by persons with red-green color blindness therefore a correspondence between the blue-yellow U.I. Scheme and the red-green colorblindness mode is determined. A further correspondence between U.I. size of the first application and Font Size of the second application may be determined. The U.I. size setting value shown is the qualitative measurement of "large" whereas the Font Size setting value shown is the quantitative measurement of "18 points". To facilitate the determination of correspondences between settings and/or setting value the first device 205 may include a database that contains a listing of application settings and the correspondences between settings of the first application and settings of a second or other application. In yet other implementations a decision tree may be used for each setting of the first application to determine the correspondence of settings between the first application and the settings of a second or other application. In some implementations, the correspondence between the settings of the two applications may be determined relative to default settings. For example, suppose the default font size for the first application is 16 point and the user has set the font size for that application to the next highest size, e.g., 24 point. If the default font size setting on the second application is 16 point and the next highest font size is 26 point, then the second application's font size setting would be updated one size up from default, i.e., from 16 point to 26 point. Furthermore, it may be possible for an application to detect the actual font size of the default setting or chosen setting, even if one application describes a font size merely as Small, Medium, or Large, such settings may correspond to on a point value. Once correspondence between the settings of the first application 206 and the settings of the second application 202 have been determined some setting values may be directly imported. As shown in the illustrated example, the setting value enabling the on-screen keyboard is directly imported from the second device.

In some optional implementations the setting or setting value from the second application may be modified to be compatible with the first application. As shown in the example the Font Size setting of the second application 202 which corresponds to U.I size of the first application 206 has the setting value of 18 pts modified to Large U.I. Size in the first application 206. In the other example shown the U.I. color scheme is determined to correspond to the color blindness mode and the setting value of U.I. Color Scheme in the second application 202 of Blue-Yellow is modified to be Red-Green for the Color Blindness mode setting of the first application 206.

Figure 3:
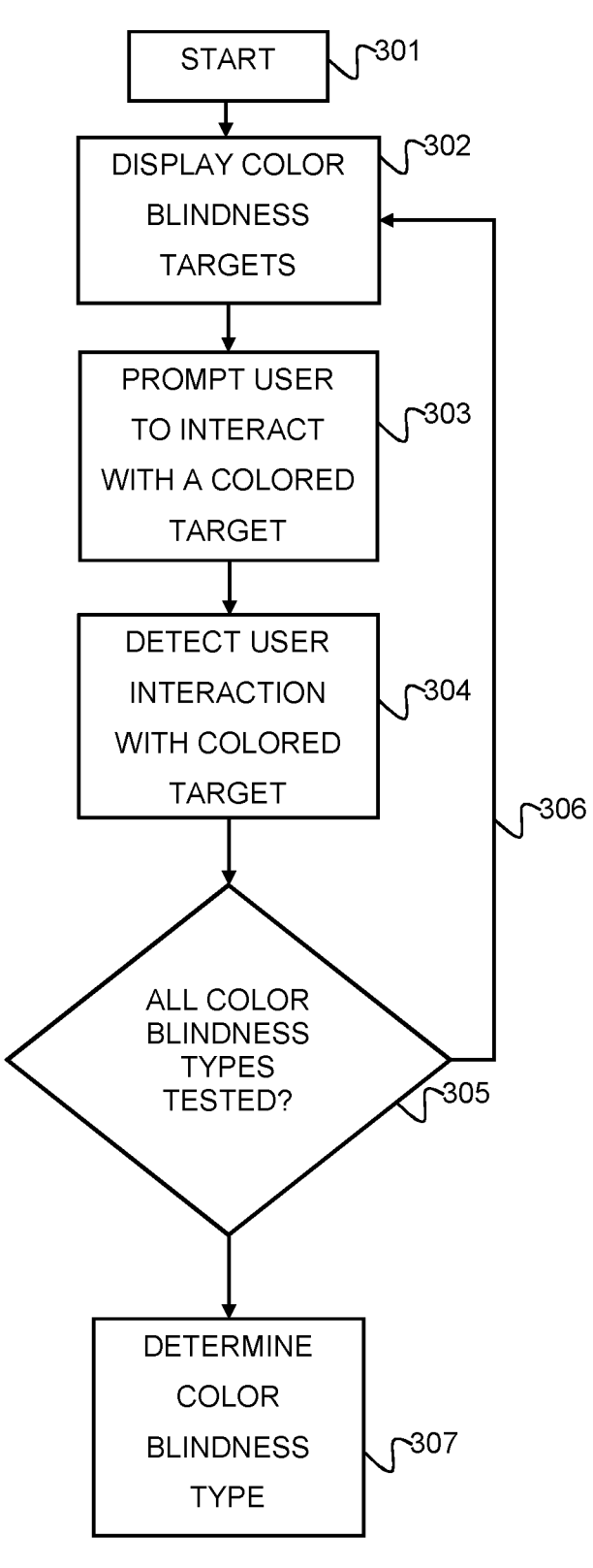
FIG. 3 is a flow diagram showing a visual test game for testing color blindness according to an aspect of the present disclosure.
Figure 4:
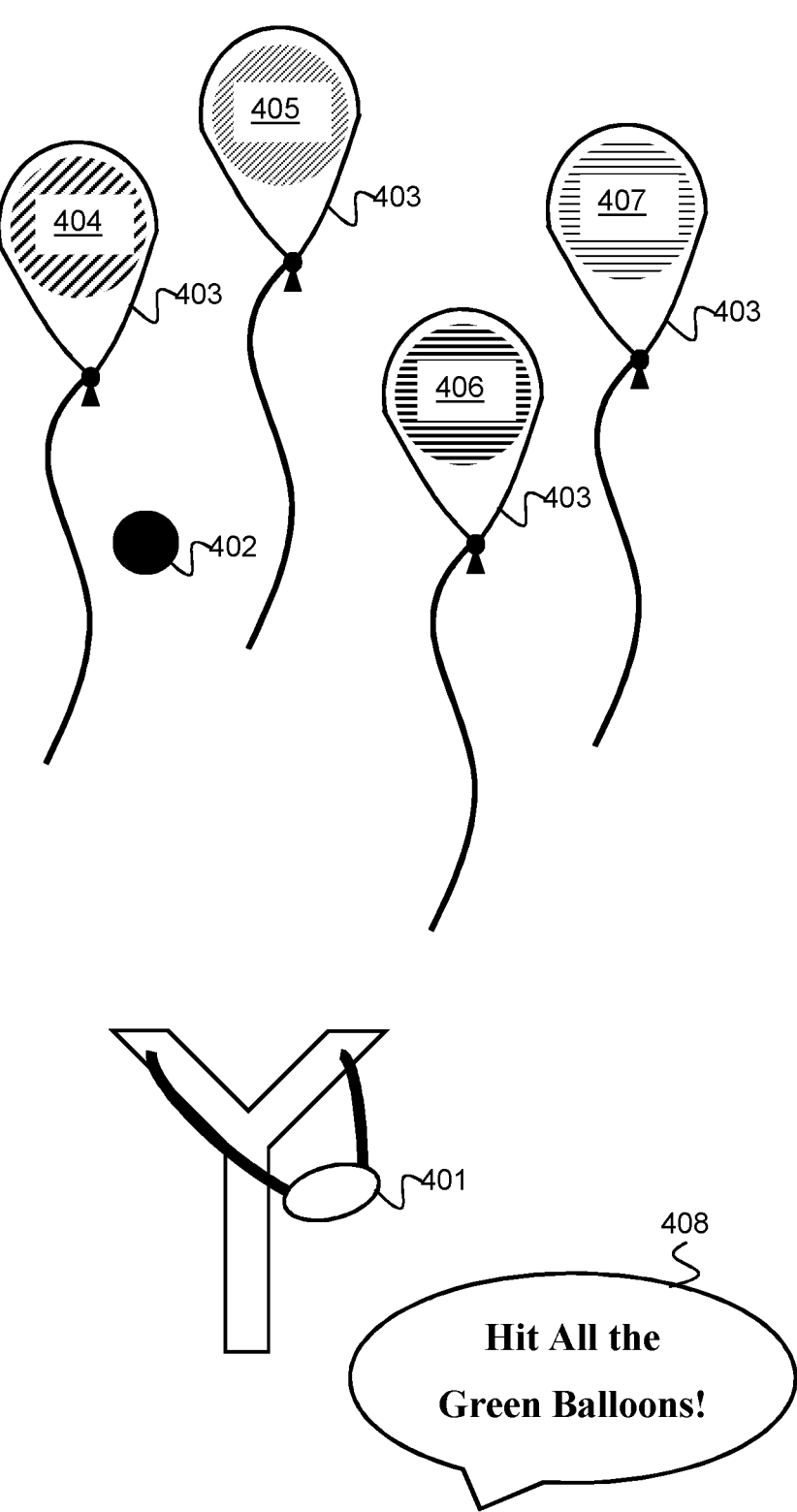
FIG. 4 is a pictorial diagram of an example of a color blindness vision test game according to aspects of the present disclosure.

In some implementations the second application may include a visual test game. The visual test game may be part of a video game or other application, such as an operating system. In some implementations the visual test game may be a stand-alone application. In other implementations, the visual test game (the second application) and the first application may be subroutines of a common application. FIG. 3 is a flow diagram showing a visual test game for testing color blindness according to an aspect of the present disclosure. The color blindness test game may use colored targets to detect the type of color blindness of the user. In the implementation shown a user or another application may start 301 a color blindness test game. In the color blindness test game, the device may display interactable color blindness targets 302. The color blindness targets may be colored, for example and without limitation, hues that correspond to hues that a person with color blindness would have difficulty distinguishing from each other. FIG. 4 pictorially depicts an example of a color blindness vision test game according to aspects of the present disclosure. As shown in this example the color blindness test game displays balloons 403 as interactable color blindness targets. The balloons 403 may be colored different colors which correspond to hues of colors that a person with a type of color blindness would have difficulty distinguishing from each other. For example, and without limitation, a first balloon may be colored red 404, a second balloon may be colored green 405, a third balloon may be colored blue 406, and a fourth balloon may be colored yellow 407. Alternatively balloons of hues for one type of colorblindness may be displayed and each type of color blindness may be tested iteratively. By way of example and not by way of limitation, a first balloon may be colored red 404, a second balloon may be colored light green 405, a third balloon may be colored lime green 406 and a fourth balloon may be colored light red 407 to test for red-green color blindness. Additionally, the color blindness test may display one or more balloons that a person with color blindness can accurately distinguish as a control for the user randomly choosing targets. Next the device prompts the user to interact with a colored target displayed on the device as shown at element 303. In the implementation shown in FIG. 4 the user is provided with a sling shot 401 with which to interact with the balloons and prompted to interact with the color blindness targets 408 for example and without limitation, here the user is instructed to hit all of the green balloons with sling shot pebbles.

Next the device waits for and detects the user interaction with the color blindness targets as shown at 304. In the balloon example the user, releases a pebble 402 at red balloon 404 when prompted to shoot a green balloon, indicating the user may have difficulty distinguishing between red and green. After the user has interacted with a color blindness target it is determined whether every type of color blindness has been tested for as shown at 305. If all types of color blindness have not been tested, the method may repeat, displaying new color blindness targets 302, prompting the user to interact with a color target that corresponds to a different type of color blindness than previously tested 303 and detecting user interaction with the colored targets 304. Steps 302 to 305 may be repeated any number of time until all types of colorblindness have been tested or in some implementations, a threshold level of confidence is reached that the user has a type of color blindness or the user is not colorblind. Once all types of colorblindness have been tested and in some implementations a threshold confidence level for a type of color blindness or no colorblindness has been achieved, the application determines the type of colorblindness or no colorblindness result for the user as shown at 307. This result may then be provided to the first application such 207 for use with the application settings 206 such as color blindness modes.

Figure 5:
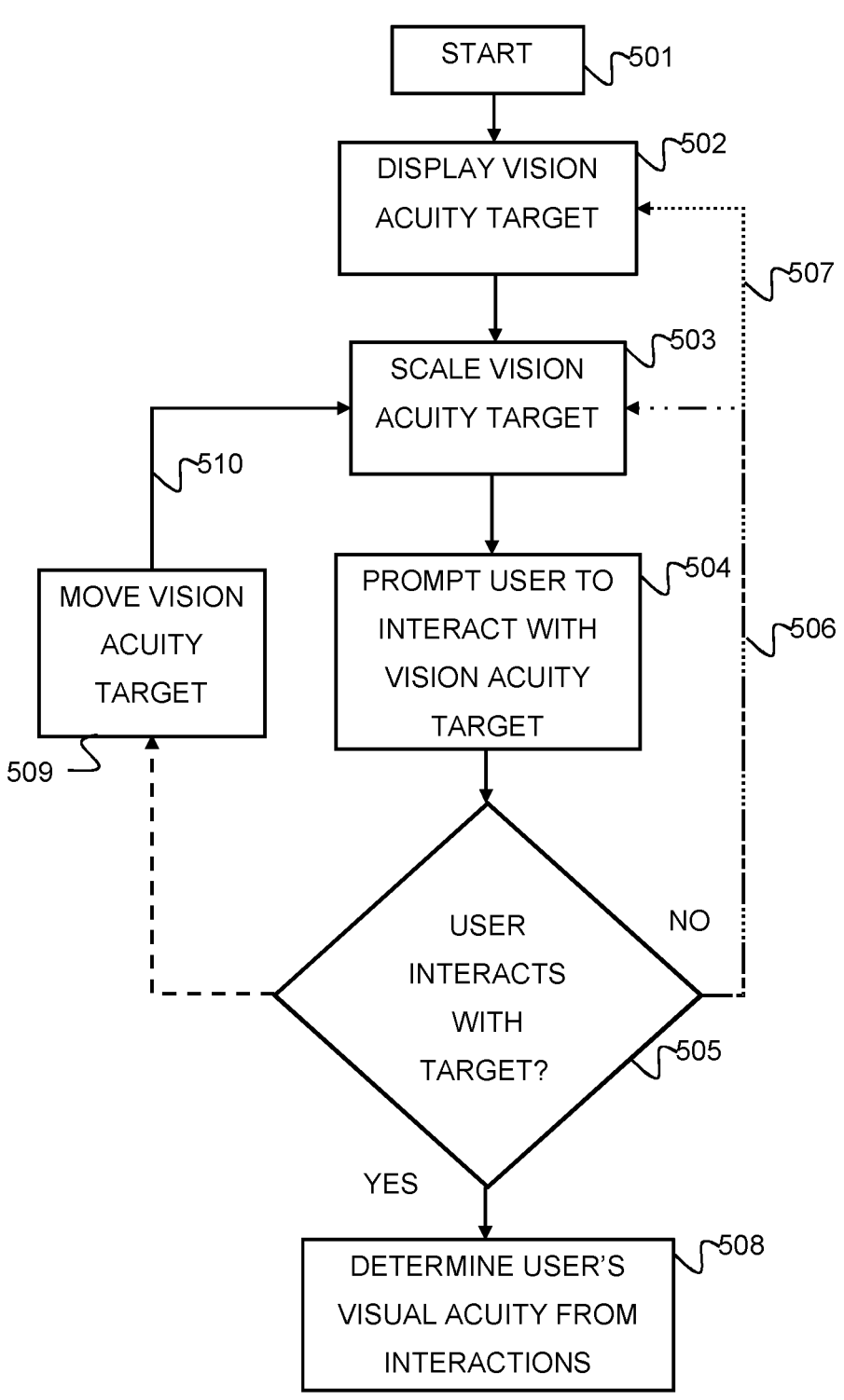
FIG. 5 is a flow diagram showing a visual test game for testing visual acuity according to an aspect of the present disclosure.

FIG. 5 is a flow diagram showing a visual test game for testing visual acuity according to an aspect of the present disclosure. The visual acuity test game may use a moving target that changes size to detect the visual acuity of the user. In the implementation shown a user or another application may start a visual acuity test game at 501. In the visual acuity test game, the user may be instructed to follow the path of a vision acuity test target that starts out small and increases in size as the test progresses. Initially the system running the visual acuity test game displays a vision acuity test target 502. The vision acuity test target may then be scaled 503 to test the visual acuity of the user. In some implementations the vision acuity test target may be scaled before it is displayed for the first time, this may prevent the user from initially seeing the test target.

Figure 6:
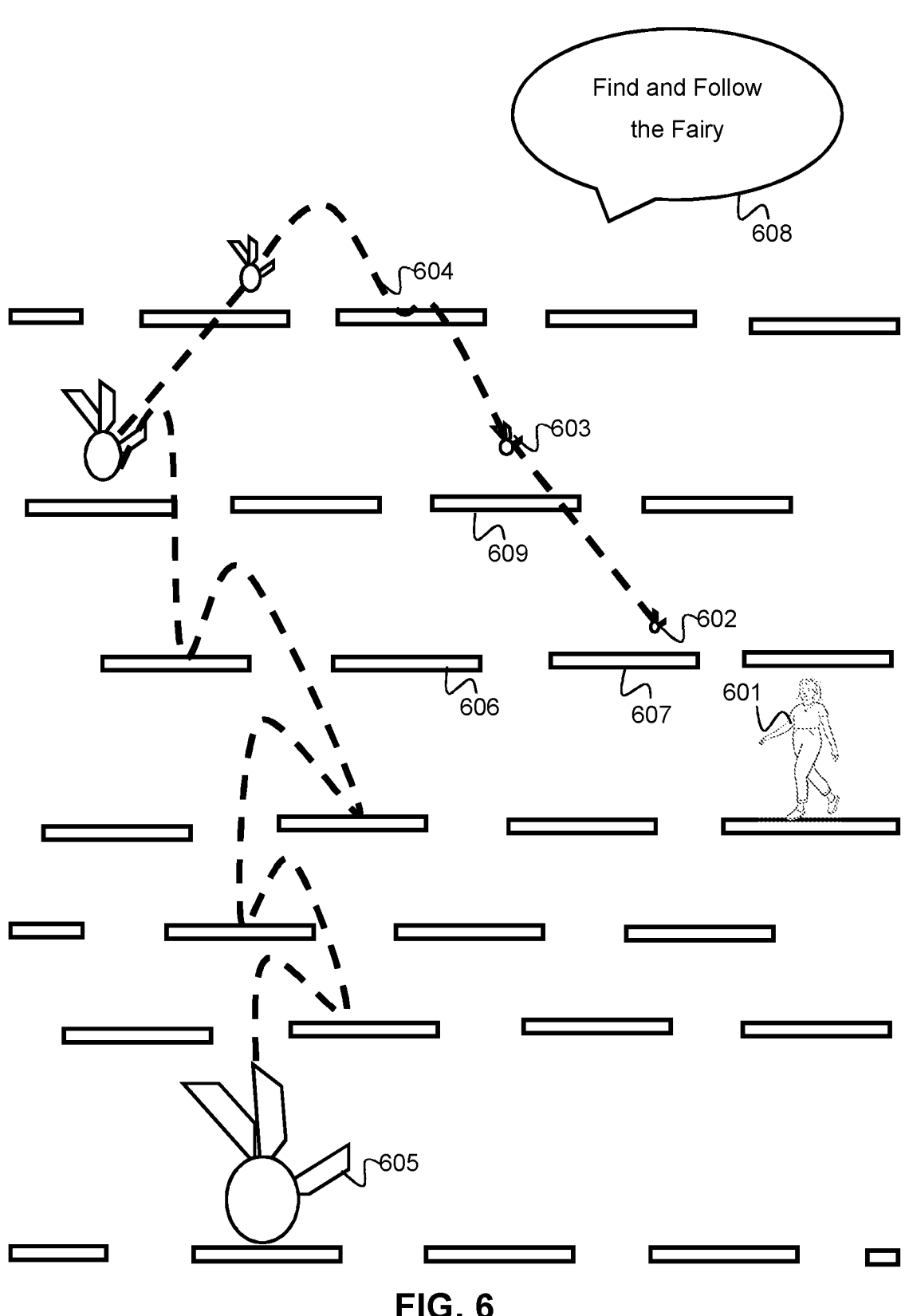
FIG. 6 is a pictorial diagram of an example of the visual acuity test game according to aspects of the present disclosure.

FIG. 6 pictorially depicts an example of the visual acuity test game of FIG. 5. In the example shown, the vision acuity test target is a fairy; multiple instances of the same fairy, 602, 603, 605 are shown here to represent changes in the scaling and movement of the fairy along a path 604 as the test progresses through time. The vision acuity test target may be initially scaled to for example and without limitation a size chosen such that the vision acuity target would be imperceptible to a person sifting an average distance away from the display screen of the system and having better than average vision, e.g., a person having 20/15 vision, sifting 6 feet away from the screen. A user in this vision test game is represented by an avatar 601. After displaying the vision acuity target at 502 and scaling the visual acuity target at 503, the user is prompted to interact with the vision acuity target at 504. In the example the system displays a dialog box 608 instructing the user to find and follow the fairy with their avatar 601. The system then determines whether the user interacts with the vision acuity target at 505. In the example the user interacts with the vision target by moving to the platform 607 that the fairy is hovering above. If the user does not move or moves to a platform that the fairy is not hovering over 606, it may be determined that the user does not actually see the vision target.

If it is determined that the user is not interacting with the target the system may optionally return at 506 to scaling the vision target at 503 or return at 507 to display a different vision target at 502 and display that target. In yet some alternative implementations the system may move the vison acuity target at 509 locations within the screen after the user interacts with the target or when the user does not interact with the target and then return at 510 to scaling the target. This may ensure that the user is actually interacting with the vision acuity target and did not interact with the vision acuity target accidentally. As the test progresses the scale of the vision acuity target may be increased with each iteration until the test completes. The size of the vision acuity target may be increased until a person with only the most acute vision impairment would miss the target. The user's visual requirements may be determined by the size of the vision acuity target when the user begins interacting with the vision acuity target. In some implementations the test may finish when the user begins interacting with the vision acuity target and thus determining the visual acuity of the user at 508. Alternatively, the test may continue until the vision test target has been scaled up to its maximum size, in which case the visual acuity level of the user may be determined by when the user consistently interacts with the vision acuity target. This implementation may ensure that the user did not accidently interact with the vision acuity target. The vision acuity settings may then be imported into another application.

As shown in the Example depicted in FIG. 6, the user may jump with their avatar 601 to the platform 607 on which the fairy 602 hovers. Here, the vision acuity target, fairy 602 may be displayed and initially scaled to, for example and without limitation, a size chosen such that the vision acuity target would be imperceptible to a person sitting an average distance away from the display screen of the system and having better than average vision. To interact with the target the user may navigate their avatar 602 to platform 607 where the fairy 602 initially is hovering. If the user moves the avatar to a different platform such as platform 606 or remains still then it is determined that the user does not see the vision target at its current size. The fairy may then move on for example a predetermined path 604 or random path and the size of the fairy may be scaled up to fairy 603. As the test progresses the larger fairy 603 may hover over a new platform 609. The user may move their avatar to the platform 609 having the larger fairy 603. This may prove that the user can see the vision acuity target and thus may be correlated to the user's visual acuity. To ensure that the user sees the vision acuity target the fairy may continue to move 604 and the fairy's size may continue to be increased until the maximum test size is reached 605. The user's vision acuity setting may then be determined from the size of the vision acuity target at which the user began consistently interacting with the target.

Figure 7:
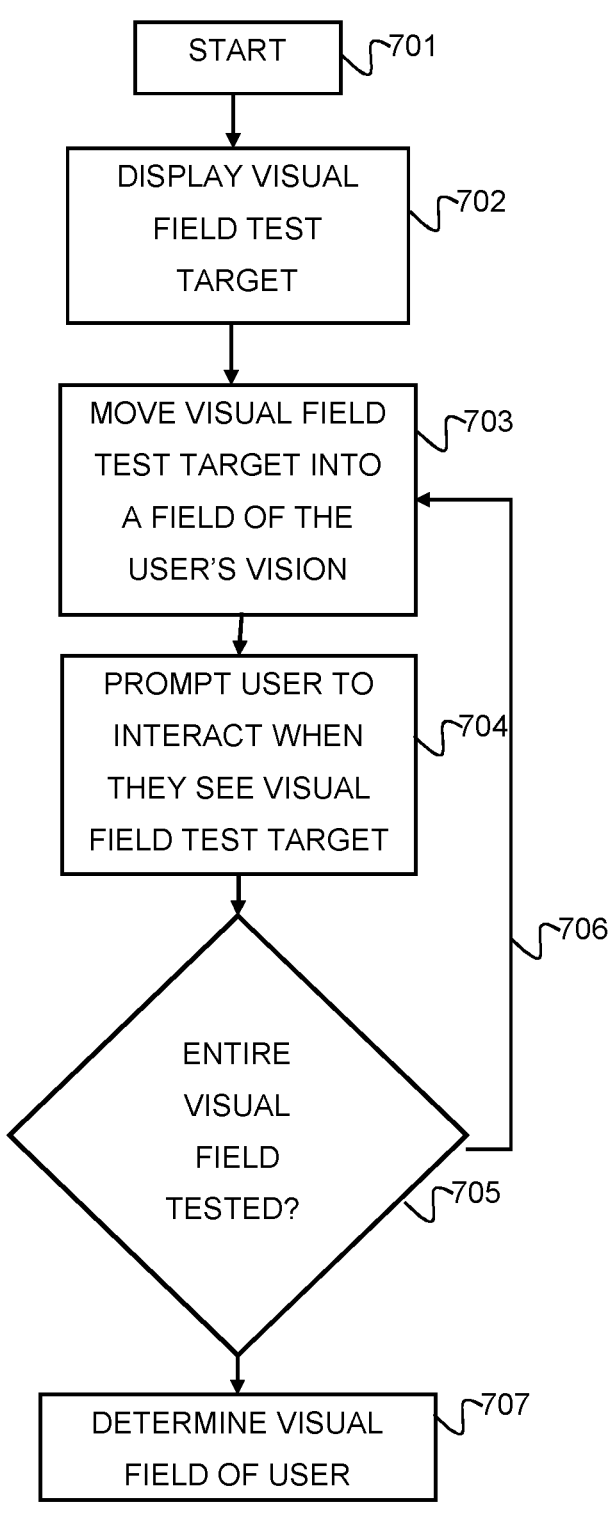
FIG. 7 is a flow diagram showing a visual test game for testing a field of vison of the user according to an aspect of the present disclosure.

FIG. 7 is a flow diagram showing a visual test game for testing a field of vision of the user according to an aspect of the present disclosure. The visual field test game may use a moving target to detect problems with the field of vision of the user. In the implementation shown, a user or another application may start 701 a visual field test game. The visual test game may display a visual test field target 702. The visual field test target may be for example and without limitation an interactive sprite or three-dimensional object in a virtual space. It may be advantageous for the visual field test game to be performed using a display that is a fixed distance from the user's head such as a head mounted display. The visual field test target may then be moved into a field of vision of the user 703. In some implementations the user may be instructed to affix their vision on a point within the display, to aid in affixation of the user's vision an object such as a target or fly may be displayed in the center of the display and the user may be instructed to affix their vision onto that target. The user may then be instructed to interact with the application when they see the visual field test target 704. The user interaction may be for example and without limitation a button press, key press, joystick movement or similar. The test may continue 706 moving the visual field test target around the user's field of vision of the user's vision until the entire field of vision of the user is tested 705. Once the entire field of view has been tested it may be determined whether the user has any field of view problems. A user's field of view may be represented by a 155-degree horizontal arc and 135-degree vertical arc creating a cone of vision that extends 95 degrees from center towards the ear of the user and 60 degrees from center toward the nose of the user, 60 degrees above center and 75 degrees below center. Additionally, near the central retinae of each eye 15 degrees offset from center toward the ear there is a blind spot created by the connection of the eye to the brain, known as the optic nerve. By way of example and without limitation, if the visual field target is moved to an area 30 degrees from center of the user's left eye and the user does not interact with the application then it may be determined that the user has a blind spot in that area.

System

Figure 8:
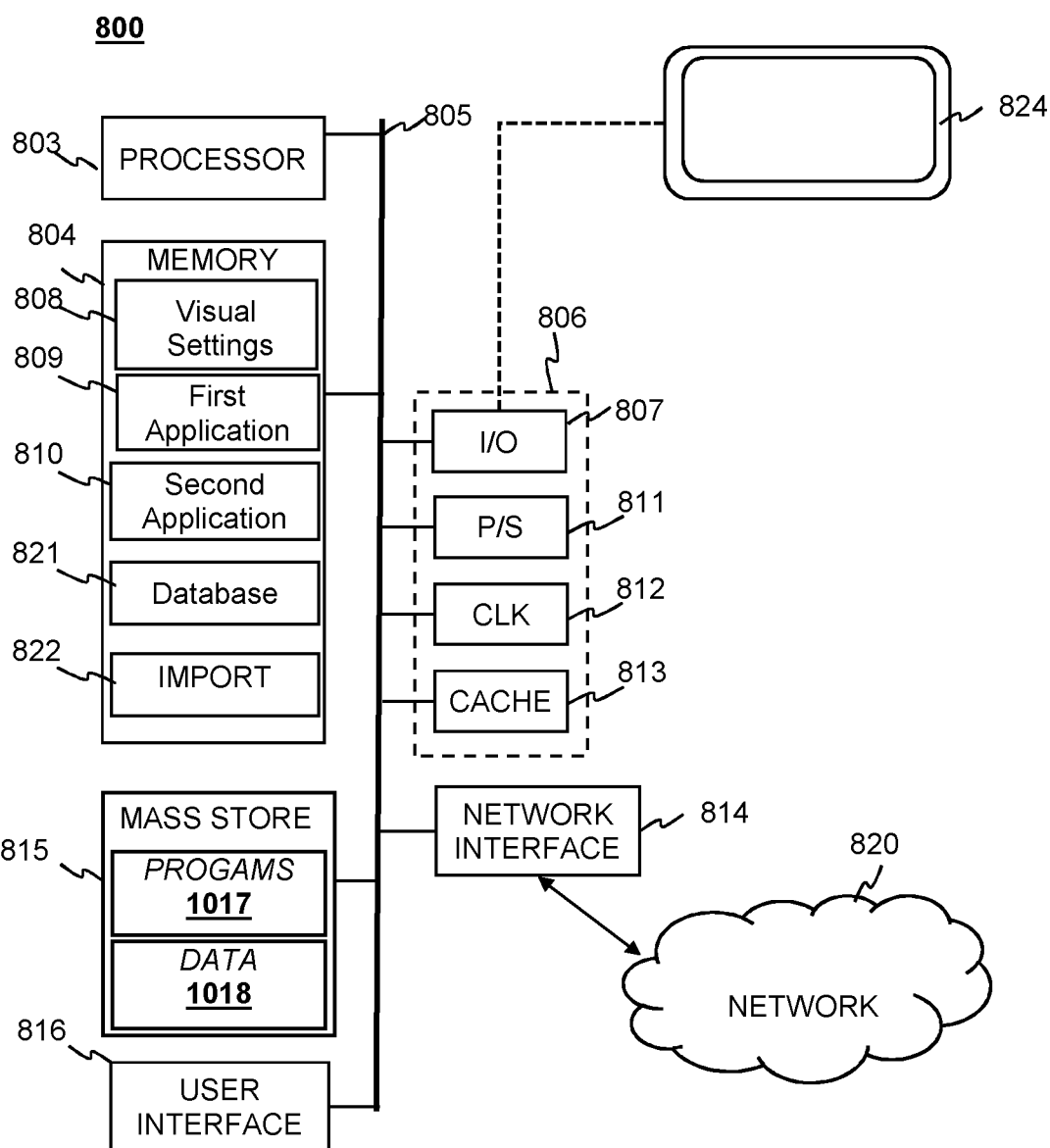
FIG. 8 is a block system diagram for a system automated detection of visual impairment and adjustment of settings for visual impairment according to aspects of the present disclosure.

FIG. 8 is a block system diagram for automated detection of visual impairment and adjustment of settings for visual impairment according to aspects of the present disclosure. By way of example, and not by way of limitation, according to aspects of the present disclosure, the system 800 may be an embedded system, mobile phone, personal computer, tablet computer, portable game device, workstation, game console, and the like.

The system 800 generally includes a central processor unit (CPU) 803, and a memory 804. The system 800 may also include well-known support functions 806, which may communicate with other components of the system, e.g., via a data bus 805. Such support functions may include, but are not limited to, input/output (I/O) elements 807, power supplies (P/S) 811, a clock (CLK) 812 and cache 813.

The system 800 may include a display device to present rendered graphics to a user. In alternative implementations, the display device may be a head mounted display 824 used in conjunction with the system, 800 and for testing of the user's field of vision. The display device may be in the form of a flat panel display, head mounted display (HMD), cathode ray tube (CRT) screen, projector, or other device that can display visible text, numerals, graphical symbols, or images.

The system 800 includes a mass storage device 815 such as a disk drive, CD-ROM drive, flash memory, solid state drive (SSD), tape drive, or the like to provide non-volatile storage for programs and/or data. The system 800 may also optionally include a user interface unit 816 to facilitate interaction between the system 800 and a user. The user interface 816 may include a keyboard, mouse, joystick, light pen, game pad or other device that may be used in conjunction with a graphical user interface (GUI). The system 800 may also include a network interface 814 to enable the device to communicate with other devices over a network 820. The network 820 may be, e.g., a local area network (LAN), a wide area network such as the internet, a personal area network, such as a Bluetooth network or other type of network. These components may be implemented in hardware, software, or firmware, or some combination of two or more of these.

The CPU 803 may include one or more processor cores, e.g., a single core, two cores, four cores, eight cores, or more. In some implementations, the CPU 803 may include a GPU core or multiple cores of the same Accelerated Processing Unit (APU). The memory 804 may be in the form of an integrated circuit that provides addressable memory, e.g., random access memory (RAM), dynamic random-access memory (DRAM), synchronous dynamic random-access memory (SDRAM), and the like. The main memory 804 may include a first application 809 used by the processor 8003 while processing. The main memory 804 may also include visual settings 808 used during processing of the first application 809. In some implementation a second application 810 may also be stored in memory and processed by the processor 803 while the first application is also being processed. Alternatively, the second application may be running on a second device in communication with the system 800. The second application 810 may include a vision test game such as one or more of the vision test games described in FIGS. 3-7. Additionally, the Memory 804 may include a database 821 of setting correspondences for the first application and other applications. The Memory 804 may further include a setting importation program 822 configured to cause the processor to carry out the method for setting importation as shown in FIG. 1.

The Mass Storage 815 may contain Application or Programs 817 that are loaded in to the main memory 804 when processing begins on the application 823. Additionally, the mass storage 815 may contain data 818 used by the processor during processing of the first application 809 and second application 810, generating the visual settings 808, importation of visual settings 822 and filling the database 821.

Aspects of the present disclosure provide for automated adjustment of visual settings for computer programs and systems. Persons with visual impairment, even those who might not be aware of such impairments, can benefit from the convenience of such automation.

While the above is a complete description of the preferred embodiment of the present invention, it is possible to use various alternatives, modifications and equivalents. Therefore, the scope of the present invention should be determined not with reference to the above description but should, instead, be determined with reference to the appended claims, along with their full scope of equivalents. Any feature described herein, whether preferred or not, may be combined with any other feature described herein, whether preferred or not. In the claims that follow, the indefinite article "A", or "An" refers to a quantity of one or more of the item following the article, except where expressly stated otherwise. The appended claims are not to be interpreted as including means-plus-function limitations, unless such a limitation is explicitly recited in a given claim using the phrase "means for."

What is claimed is:

1. A method for automated visual setting importation with a first application running on a first device, comprising:
   identifying a vision setting for a second application, wherein the vision setting for the second application is determined based on a vision test videogame, and the vision test videogame further comprises a color blindness test game;
   determining a vision setting of the first application corresponding to the vision setting for the second application;
   mapping a value of the vision setting for the second application to a disparate type of the vision setting of the first application;
   adjusting the vision setting for the first application based at least in part on the disparate type of the vision setting of the first application; and
   rendering visuals on the first application tailored to the vision setting for the second application by applying the vision setting determined based on the vision test videogame.

2. The method of claim 1 wherein applying the vision setting includes modifying the vision setting for the second application to be compatible with the vision setting of the first application and wherein applying the vision setting from the second application includes applying a modified vision setting to the vision setting of the first application.

3. The method of claim 1 wherein the first application is a first operating system running on a first device.

4. The method of claim 3 wherein the second application is a second operating system running on a second device.

5. The method of claim 1 wherein the color blindness test game includes prompting a user to interact with one or more colored targets displayed on the first device, determining a color blindness setting from a user interactions with the one or more colored targets.

6. The method of claim 1 wherein the vision test videogame includes a visual acuity test game.

7. The method of claim 6 wherein the visual acuity test game includes prompting a user to interact with a visual acuity target, displaying a visual acuity target on the first device, scaling the visual acuity target until the user interacts with the visual acuity target and determining from the user interacting with the visual acuity target a visual acuity setting.

8. The method of claim 1 wherein the vision test videogame includes a visual field test game.

9. The method of claim 8 wherein the visual field test game includes displaying one or more visual field test targets in a visual field to a user on the first device, prompting the user to interact with the one or more visual field test targets and determining a visual field setting from a resulting user interaction with the one or more visual field test targets.

10. The method of claim 1 wherein the vision setting of the first application includes text size, magnification, alternative color schemes for color blindness, visual field customizations, or screen resolution.

11. The method of claim 1 wherein the first application running on the first device is associated with a first user and the second application is associated with the first user or an account used by the first user.

12. A system for automated detection of visual impairment, comprising:

a processor;

a memory coupled to the processor;

non-transitory instructions included in the memory that are configured to cause the processor to carry out a method for automated visual setting importation with a first application when executed by the processor, the method comprising:

identifying a vision setting for a second application, wherein the vision setting for the second application is determined based on a vision test videogame, and the vision test videogame further comprises a color blindness test game;

determining a vision setting of the first application corresponding to the vision setting for the second application;

mapping a value of the vision setting for the second application to a disparate type of the vision setting of the first application;

adjusting the vision setting for the first application based at least in part on the disparate type of the vision setting of the first application; and rendering visuals on the first application tailored to the vision setting for the second application by applying the vision setting determined based on the vision test videogame.

13. The system of claim 12 further comprising modifying the vision setting from the second application to be compatible with the vision setting of the first application and wherein applying the vision setting from the second application includes applying the modified vision setting to the vision setting of the first application.

14. The system of claim 12 wherein the first application is a first operating system running on processor.

15. The system of claim 14 wherein the second application is a second operating system running on a second device.

16. The system of claim 12 wherein the color blindness test game includes prompting a user to interact with one or more colored targets displayed with the processor, determining a color blindness setting from a user interactions with the one or more colored targets.

17. The system of claim 12 wherein the vision test videogame includes a visual acuity test game.

18. The system of claim 17 wherein the visual acuity test game includes prompting a user to interact with a visual acuity target, displaying a visual acuity target with the processor, scaling the visual acuity target until the user interacts with the visual acuity target and determining from the user interacting with the visual acuity target a visual acuity setting.

19. The system of claim 12 wherein the vision test videogame includes a visual field test game.

20. The system of claim 19 wherein the visual field test game includes displaying one or more visual field test targets in a visual field to a user with the processor, prompting the user to interact with the one or more visual field test targets and determining a visual field setting from a resulting user interaction with the one or more visual field test targets.

21. The system of claim 12 wherein the vision setting comprises: text size, magnification, alternative color schemes for color blindness, visual field customizations, or screen resolution.

22. The system of claim 12 wherein the first application running on the processor is associated with a first user and the second application is associated with the first user or an account used by the first user.

23. A computer-readable medium having non-transitory instructions embodied thereon, the non-transitory instructions being configured to cause a computer to carry out a method for automated visual setting importation with a first application when executed by the computer, the method comprising:

identifying a vision setting for a second application, wherein the vision setting for the second application is determined based on a vision test videogame, and the vision test videogame further comprises a color blindness test game;

determining a vision setting of the first application corresponding to the vision setting for the second application;

mapping a value of the vision setting for the second application to a disparate type of the vision setting of the first application;

adjusting the vision setting for the first application based at least in part on the disparate type of the vision setting of the first application; and rendering visuals on the first application tailored to the vision setting for the second application by applying the vision setting determined based on the vision test videogame.

24. The method of claim 1, wherein the mapping comprises converting between qualitative and quantitative representations.

* * * * *